United States Patent
Ralph et al.

(10) Patent No.: US 10,286,504 B2
(45) Date of Patent: May 14, 2019

(54) SYNTHESIS OF PARACETAMOL (ACETAMINOPHEN) FROM BIOMASS-DERIVED P-HYDROXYBENZAMIDE

(71) Applicant: Wisconsin Alumni Research Foundation, Madison, WI (US)

(72) Inventors: John Ralph, Madison, WI (US); Steven Karlen, Verona, WI (US); Justin Mobley, Cottage Grove, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/914,597

(22) Filed: Mar. 7, 2018

(65) Prior Publication Data

US 2018/0258030 A1    Sep. 13, 2018

Related U.S. Application Data

(60) Provisional application No. 62/468,420, filed on Mar. 8, 2017.

(51) Int. Cl.

| | |
|---|---|
| *C07C 213/02* | (2006.01) |
| *C07C 231/10* | (2006.01) |
| *B23P 19/04* | (2006.01) |
| *B60L 11/18* | (2006.01) |
| *H01M 8/10* | (2016.01) |
| *H01M 16/00* | (2006.01) |
| *H01M 8/04858* | (2016.01) |
| *B60K 3/02* | (2006.01) |
| *B60K 15/03* | (2006.01) |
| *G05D 23/19* | (2006.01) |

(52) U.S. Cl.
CPC ............ *B23P 19/04* (2013.01); *B60K 3/02* (2013.01); *B60K 15/03006* (2013.01); *B60L 11/1816* (2013.01); *B60L 11/1827* (2013.01); *B60L 11/1838* (2013.01); *B60L 11/1851* (2013.01); *B60L 11/1881* (2013.01); *C07C 213/02* (2013.01); *C07C 231/10* (2013.01); *G05D 23/1904* (2013.01); *H01M 8/04925* (2013.01); *H01M 8/10* (2013.01); *H01M 16/006* (2013.01); *B60K 2015/03019* (2013.01); *B60K 2015/03026* (2013.01); *C07B 2200/09* (2013.01); *H01M 2220/20* (2013.01); *H01M 2250/20* (2013.01); *Y02B 90/12* (2013.01); *Y02T 10/7005* (2013.01); *Y02T 90/32* (2013.01)

(58) Field of Classification Search
None
See application file for complete search history.

(56) References Cited

U.S. PATENT DOCUMENTS

| | | | | |
|---|---|---|---|---|
| 4,264,525 | A * | 4/1981 | Huber, Jr. | C07C 233/16 564/223 |
| 4,565,890 | A * | 1/1986 | Sathe | C07C 233/16 564/216 |
| 5,155,269 | A * | 10/1992 | Dunn | C07C 213/10 564/137 |
| 5,155,273 | A * | 10/1992 | Fritch | C07C 231/10 564/223 |
| 2014/0371418 | A1* | 12/2014 | Ng | C12N 9/1085 528/84 |

OTHER PUBLICATIONS

Bradshaw TC, Alizadeh H, Teymouri F, Balan V, Dale BE, "Ammonia fiber expansion pretreatment and enzymatic hydrolysis on two different growth stages of reed canarygrass," *Appl Biochem Biotechnol.* 2007, 136:395-405.
"Chemical Profile: Acetaminophen," (Dec. 2, 2005) *ICIS Chemical Business* 12:22, available online at https://www.icis.com/resources/news/2005/12/02/510381/chemical-profile-acetaminophen/.
Da Costa Sousa, Leonardo et al. (2016) "Next-generation ammonia pretreatment enhances cellulosic biofuel production," *Energy Environ. Sci.*, 9:1215-1223.
Mosier N, Wyman C, Dale BE, Elander R, Lee YY, Holtzapple M, Ladisch M: "Features of promising technologies for pretreatment of lignocellulosic biomass," *Bioresource Technol.* 2005, 96:673-686.
Murnen HK, Balan V, Chundawat SPS, Bals B, Da Costa Sousa L, Dale BE, "Optimization of ammonia fiber expansion (AFEX) pretreatment and enzymatic hydrolysis of Miscanthus × giganteus to fermentable sugars," *Biotechnol Prog.* 2007, 23:846-850.
Teymouri F, Laureano-Perez L, Alizadeh H, Dale B: "Optimization of the ammonia fiber explosion (AFEX) treatment parameters for enzymatic hydrolysis of corn stover," *Bioresource Technol*, 2005, 96:2014-2018.

\* cited by examiner

*Primary Examiner* — Amy C Bonaparte
(74) *Attorney, Agent, or Firm* — Joseph T. Leone, Esq.; DeWitt LLP

(57) ABSTRACT

Disclosed is a method to make N-acetyl-p-aminophenol. The method includes steps for converting biomass-derived p-hydroxybenzoates to p-hydroxybenzamide, then to p-aminophenol; and then N-acetylating the p-aminophenol.

21 Claims, No Drawings

SYNTHESIS OF PARACETAMOL (ACETAMINOPHEN) FROM BIOMASS-DERIVED P-HYDROXYBENZAMIDE

CROSS-REFERENCE TO RELATED APPLICATIONS

Priority is hereby claimed to provisional application Ser. No. 62/468,420, filed Mar. 8, 2017, which is incorporated herein by reference.

FEDERAL FUNDING STATEMENT

This invention was made with government support under DE-FC02-07ER64494 awarded by the US Department of Energy. The government has certain rights in this invention.

BACKGROUND

Paracetamol (acetaminophen; N-acetyl-p-aminophenol; APAP) is an analgesic and fever-reducing medicine:

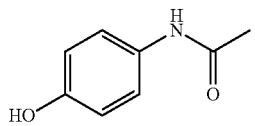

It is an active ingredient in many widely sold over-the-counter medicines, such as Tylenol and Panadol. As a prescription pharmaceutical it is also sold in combination with opioid pain medications for treating more severe pain. It is the most commonly used medication for pain and fever in the United States. It is on the World Health Organizations List of Essential Medicines.

Introduced in the early 1900s, acetaminophen is a coal tar derivative that acts by interfering with the synthesis of prostaglandins and other substances necessary for the transmission of pain impulses. Although its action is similar to that of aspirin, it lacks aspirin's anti-inflammatory and blood-thinning effects, is less irritating to the stomach, and can be used by people who are allergic to aspirin. Heavy use has been linked to an increased incidence of liver failure, especially in alcoholic patients.

The original synthesis starts with phenol, which is nitrated with sodium nitrate to yield a mixture of ortho- and para-nitrophenol. These are then separated by distillation. The nitro group of the para-nitrophenol is then reduced to an amine, giving para-aminophenol. The amine is then acetylated with acetic anhydride:

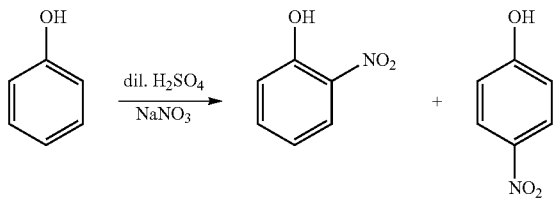

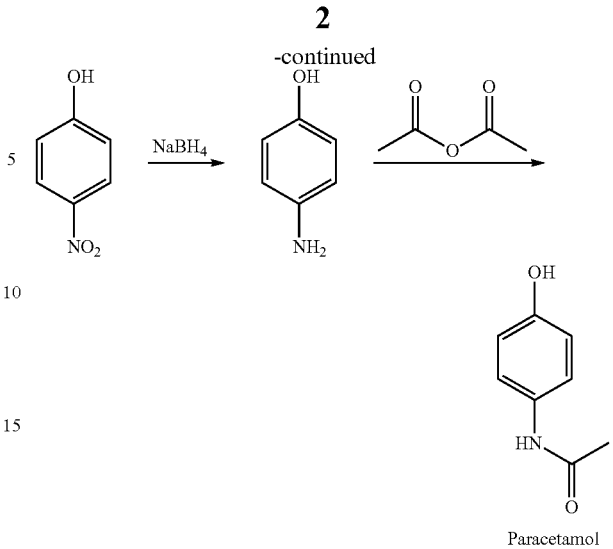

An alternative industrial synthesis uses direct acylation of phenol with acetic anhydride. The resulting ketone is then converted to a ketoxime with hydroxylamine, followed by an acid-catalyzed Beckmann rearrangement to give the desired amide product:

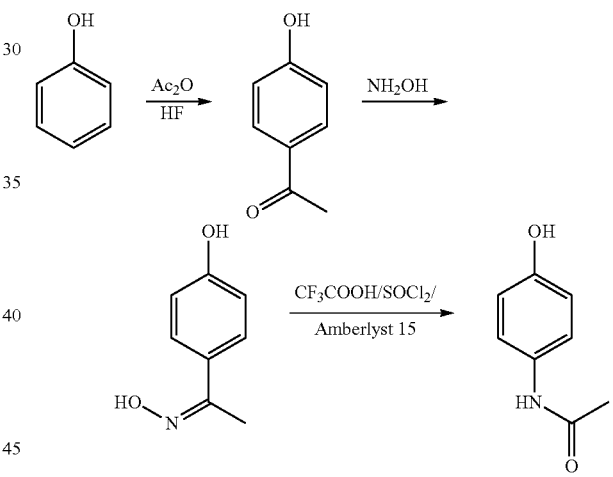

In both approaches, the starting reactant, phenol, is derived from fossil fuels. There remains a long-felt and unmet need for a method to make paracetamol from a renewable feedstock.

SUMMARY

Disclosed is a method to make N-acetyl-p-aminophenol. The method comprises converting p-hydroxybenzamide to p-aminophenol; and then N-acetylating the p-aminophenol. It is preferred that the p-hydroxybenzamide is derived from natural p-hydroxybenzoate esters found in various biomass sources.

The first step can be achieved by contacting the p-hydroxybenzamide with a hypohalite salt, such as sodium hypochlorite (NaOCl), sodium hypobromite (NaOBr), or sodium hypoiodite (NaOI) to cause a Hofmann-style rearrangement reaction yielding p-aminophenol. The resulting p-aminophenol is then acetylated to yield N-acetyl-p-aminophenol. This can be done, for example, by contacting the p-aminophenol with acetic anhydride and water for a time and at a temperature to yield N-acetyl-p-aminophenol.

The preferred method yields N-acetyl-p-aminophenol (paracetamol) by contacting p-hydroxybenzamide with sodium hypochlorite (NaOCl) in an aqueous alkaline solution at a suitable temperature and for a suitable time to yield p-aminophenol via a Hofmann-type reaction; and then contacting the p-aminophenol with acetic anhydride and water for a time and at a temperature to yield N-acetyl-p-aminophenol.

DETAILED DESCRIPTION

Disclosed herein is an inexpensive method for producing paracetamol (acetaminophen) from p-hydroxybenzamide. A notable feature of the method is that p-hydroxybenzamide can produced from p-hydroxybenzoate. p-Hydroxybenzoate can be produced from lignin sourced from a number of biomass species, most significantly species of poplar and aspen, willow, and palm. p-Hydroxybenzamide is produced when such biomass is treated with ammonia in the ammonia fiber expansion process (AFEX) or the extractive ammonia process (EA). See Reaction Scheme 1:

nia is added to the biomass under moderate pressure (about 100 to about 400 psi; about 0.69 to 2.76 MPa) and temperature (about 70 to about 200° C.) before rapidly releasing the pressure. The major process parameters are the temperature of the reaction, residence time, ammonia loading, and water loading. AFEX decrystallizes cellulose, hydrolyzes hemicellulose, removes and depolymerizes lignin, and increases the size and number of micropores in the cell wall. As a result, the rate of subsequent enzymatic hydrolysis is greatly increased. See Mosier N, Wyman C. Dale BE, Elander R, Lee Y Y, Holtzapple Ladisch M: "Features of promising technologies for pretreatment of lignocellulosic biomass," *Bioresource Technol.* 2005, 96:673-686, AFEX gives near-theoretical yields of glucose on different types of agricultural residues and energy crops. See Teymouri F, Laureano-Perez L, Alizadeh H, Dale B: "Optimization of the ammonia fiber explosion (AFEX) treatment parameters for enzymatic hydrolysis of corn stover," *Bioresource Technol.* 2005, 96:2014-2018; Murnen H K, Balan V, Chundawat S P S, Bals B, da Costa Sousa L, Dale B E, "Optimization of ammonia fiber expansion (AFEX) pretreatment and enzymatic hydrolysis of Miscanthus x giganteus to fermentable Reaction Scheme 1: p-hydroxybenzamide derived from biomass containing p-hydroxybenzoate:

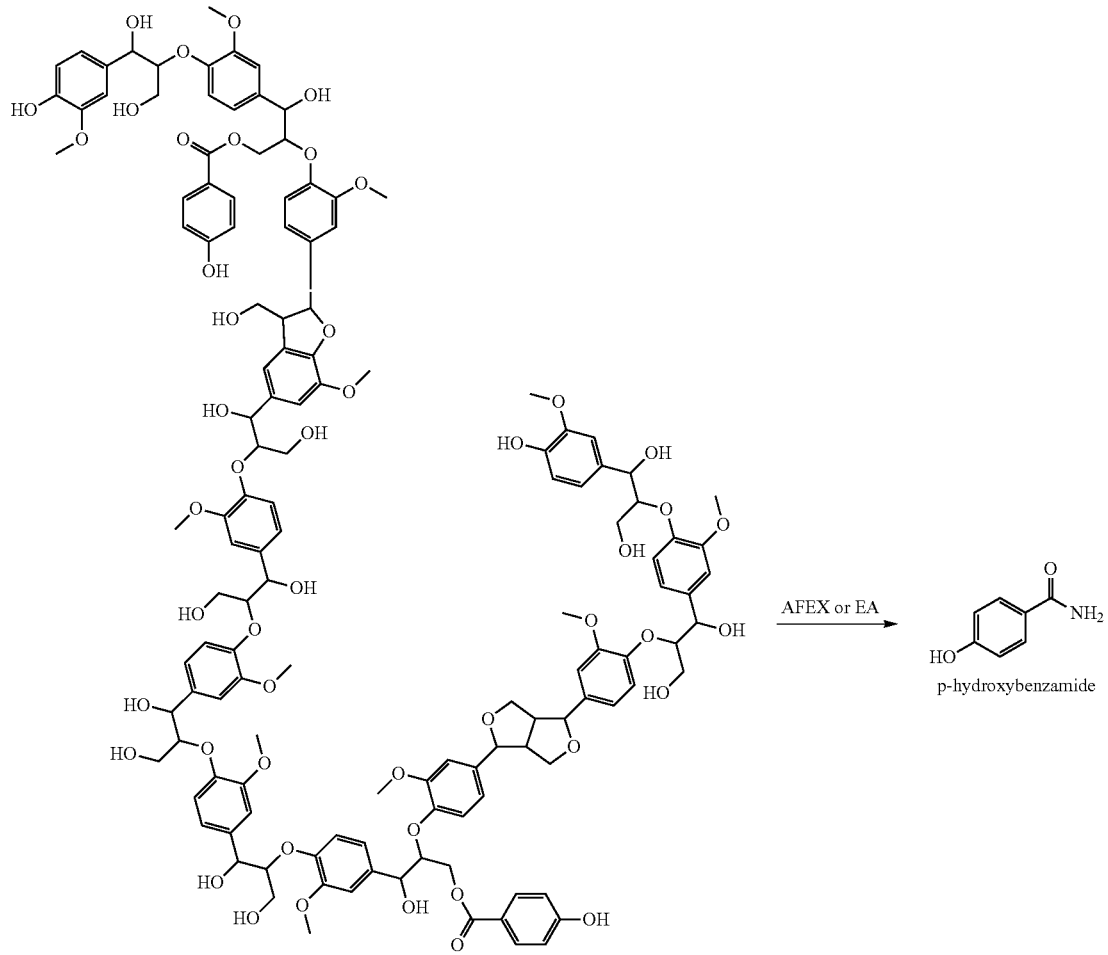

The AFEX process is a method for pretreating agricultural material for bioenergy production. In AFEX, liquid ammosugars," *Biotechnol Prog.* 2007, 23:846-850; and Bradshaw T C, Alizadeh H, Teymouri F, Balan V, Dale B E, "Ammonia fiber expansion pretreatment and enzymatic hydrolysis on two different growth stages of reed canarygrass," *Appl Biochem Biotechnol.* 2007, 136:395-405.

The EA pretreatment likewise uses ammonia, but is a three-stage process: reaction; extraction; and product/solvent recovery. In the reaction phase, liquid ammonia and biomass are combined in a reactor at a sufficiently high loading to fully immerse the biomass at a defined temperature and residence time. Unlike AFEX, water is not added, so the reaction proceeds at much lower moisture levels. The reaction is heated.

As temperature increases, ammonia pressure builds up in the reactor until a new vapor-liquid equilibrium is established. During this stage, a cellulose-ammonia complex is formed, ester bonds are cleaved, and lignin is partly solubilized in the liquid ammonia phase. Similar to the AFEX process, EA pretreatment promotes ammonolysis of cell wall ester crosslinks that are particularly abundant in monocots. These key reactions disrupt lignin-polysaccharide crosslinks, thereby enabling biomass deconstruction by improving access of enzymes to embedded structural carbohydrates.

The EA-pretreated biomass is then filtered to separate the ammonia-soluble components from residual solids. During this stage, lignin is extracted, and CIII—a highly digestible cellulose allomorph—is formed from the cellulose-ammonia complex. Ammonia is continuously removed from the product stream and recycled. Nitrogen overpressure is used to maintain ammonia in the liquid state at constant temperature.

EA simultaneously converts native crystalline cellulose to a highly digestible cellulose allomorph and selectively extracts up to about 45% of the lignin from lignocellulosic biomass with near-quantitative retention of all polysaccharides. See Leonardo da Costa Sousa et al. (2016) "Next-generation ammonia pretreatment enhances cellulosic biofuel production," *Energy Environ. Sci.,* 9:1215-1223.

As of 2003, 37,000 metric tons of acetaminophen was produced in the United States alone, and nearly 80,000 metric tons were consumed world-wide. See "Chemical Profile: Acetaminophen," (2 Dec. 2005) ICIS Chemical Business 12:22, available online at https://www.icis.com/resources/news/2005/12/02/510381/chemical-profile-acetaminophen/. Compared to the current industrial process, which requires the nitration and further reduction of the petrochemically-derived phenol, the method disclosed herein utilizes a low-cost Hofmann-type reaction to achieve this conversion. The inventive method will work using p-hydroxybenzamide obtained from any source, but p-hydroxybenzamide derived from biomass is preferred. The method, a Hofmann-type rearrangement reaction, is illustrated in Reaction Scheme 2:

Reaction Scheme 1: Conversion of p-hydroxybenzamide to p-aminophenol

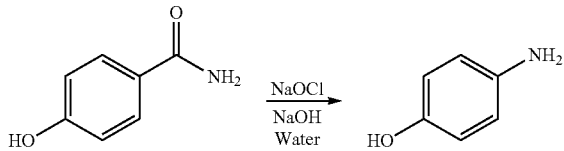

The reaction shown in Reaction Scheme 2 preferably proceeds by dissolving p-hydroxybenzamide in alkaline water. Non-aqueous solvents may also be used. Preferred pH ranges from about 10 to about 14. About 0.6 M NaOH (about pH 12.8) is preferred. To the alkaline solution of p-hydroxybenzamide is added a small excess of a hypohalite, such as sodium hypochlorite (NaOCl), sodium hypobromite (NaOBr), or sodium hypoiodite (NaOI) (~1.1 eq.). The reaction can be performed at a range of temperatures from about 20° C. to about 100° C. In the inventors' laboratory, the best results were seen at 80° C. where an 18% yield of product was obtained, with a 76% recovery of input materials (i.e., 58% recovery of starting material and 18% recover of product). The aforementioned results were obtained in 1 hour and 40 minutes. The reaction can produce a significant amount of polymeric material, especially during storage. The reaction can be performed over a considerable time range, from about 30 minutes to 24 h. The best results were seen in reactions running less than 2 h. Reaction times above and below this range are explicitly within the scope of the claimed method. Additionally, the reaction can be performed over a range of hypohalite concentrations. However, with excess equivalents more polymer is formed.

The reaction is quenched with a reducing agent, preferably 10% sodium bisulfite; Other reducing agents, such as sodium thiosulfate, will work with comparable results. The reaction mixture is neutralized with an equimolar amount of acid, for example 1 M HCl (equimolar to the amount of NaOH added in the first step). The reaction mixture is then extracted (liquid-liquid) three times with ethyl acetate. The organic extract is dried over anhydrous sodium sulfate and concentrated under vacuum.

The resulting p-aminophenol was converted to paracetamol via acylation, shown in Reaction Scheme 3:

Reaction Scheme 2: Conversion of p-aminophenol to paracetamol.

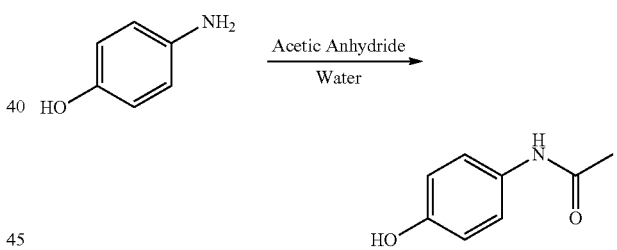

The reaction illustrated in Reaction Scheme 3 was performed at 115° C. for 10 minutes. To p-aminophenol (0.150 g), acetic anhydride (0.165 mL) and water (0.450 mL) were added. The reaction was cooled to produce crystals which were collected on a glass frit and rinsed with ice water. An 82% yield (gravimetric) was obtained.

The reaction proceeds as shown in Reaction Scheme 4:

Reaction Scheme 4: Conversions of p-aminophenol to paracetamol.

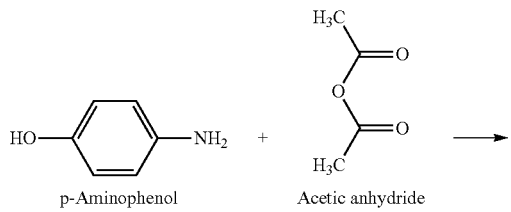

p-Aminophenol     Acetic anhydride

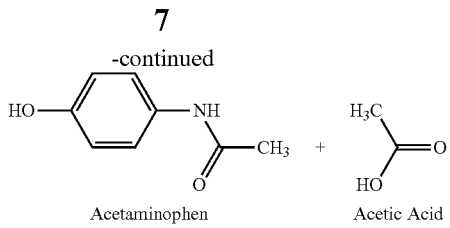

Acetaminophen    Acetic Acid

The crude solid acetaminophen contains dark impurities carried along with unreacted p-aminophenol starting material. These impurities, which are dyes of unknown structure, are formed from oxidation of the starting phenol. While the amount of the dye impurity is small, it is intense enough to impart color to the crude acetaminophen. Most of the colored impurity is destroyed by heating the crude product with sodium dithionite (sodium hydrosulfite $Na_2S_2O_3$). The dithionite reduces double bonds in the colored dye to produce colorless substances. The decolorized acetaminophen is collected on a Hirsch funnel and may optionally be further purified by crystallization.

Heat the reaction mixture at about 115° C. with stirring for about 10 minutes to complete the reaction. Once complete, cool the mixture thoroughly in an ice bath for 15-20 minutes and collect the crystals by vacuum filtration on a Hirsch funnel. To decolorize the crude product, dissolve 0.2 g of sodium dithionite (sodium hydrosulfite) in 1.5 mL of water in a 5-mL conical vial. Add the crude acetaminophen to the vial. Heat the mixture at about 100° C. for 15 minutes, with occasional stirring. Cool the mixture to precipitate the decolorized acetaminophen. To purify the decolorized product, dissolve the material in a solvent mixture composed of 50% water and 50% methanol by volume, heated to boiling. The solubility of acetaminophen in the near-boiling solvent is about 0.2 g/mL. Cool the solution to precipitate the acetaminophen.

What is claimed is:

1. A method to make N-acetyl-p-aminophenol, the method comprising:
    (a) converting p-hydroxybenzamide to p-aminophenol; and then
    (b) N-acetylating at least a portion of the p-aminophenol to yield N-acetyl-p-aminophenol.

2. The method of claim 1, wherein, step (a) comprises contacting the p-hydroxybenzamide with a hypohalite salt to cause a Hofmann-style rearrangement reaction, thereby yielding p-aminophenol.

3. The method of claim 1, wherein step (b) comprises contacting the p-aminophenol with acetic anhydride and water for a time and at a temperature to yield N-acetyl-p-aminophenol.

4. The method of claim 1, wherein step (a) comprises contacting the p-hydroxybenzamide with a hypohalite salt to cause a Hofmann-style rearrangement reaction, thereby yielding p-aminophenol; and
    step (b) comprises contacting the p-aminophenol with acetic anhydride and water for a time and at a temperature to yield N-acetyl-p-aminophenol.

5. The method of claim 4, wherein step (a) is conducted in an alkaline aqueous or non-aqueous solvent, at a pH from about 10 to about 14, a temperature from about 20° C. to about 100° C., and for a time of from about 30 minutes to about 24 h.

6. The method of claim 4, wherein step (b) is conducted at a temperature of from about 100° C. to about 150° C.

7. The method of claim 4, wherein step (a) is conducted in an alkaline aqueous or non-aqueous solvent, at a pH from about 10 to about 14, a temperature from about 20° C. to about 100° C., and for a time of from about 30 minutes to about 24 h; and
    step (b) is conducted at a temperature of from about 100° C. to about 150° C.

8. A method to make N-acetyl-p-aminophenol, the method comprising:
    (a) providing p-hydroxybenzamide derived from p-hydroxybenzoate esters derived from biomass;
    (b) converting at least a portion of the p-hydroxybenzamide to p-aminophenol; and then
    (c) N-acetylating at least a portion of the p-aminophenol to yield N-acetyl-p-aminophenol.

9. The method of claim 8, wherein, step (b) comprises contacting the p-hydroxybenzamide with a hypohalite salt to cause a Hofmann-style rearrangement reaction, thereby yielding p-aminophenol.

10. The method of claim 8, wherein step (c) comprises contacting the p-aminophenol with acetic anhydride and water for a time and at a temperature to yield N-acetyl-p-aminophenol.

11. The method of claim 8, wherein, step (b) comprises contacting the p-hydroxybenzamide with a hypohalite salt to cause a Hofmann-style rearrangement reaction, thereby yielding p-aminophenol; and
    step (c) comprises contacting the p-aminophenol with acetic anhydride and water for a time and at a temperature to yield N-acetyl-p-aminophenol.

12. The method of claim 11, wherein step (b) is conducted in an alkaline aqueous or non-aqueous solvent, at a pH from about 10 to about 14, a temperature from about 20° C. to about 100° C., and for a time of from about 30 minutes to about 24 h.

13. The method of claim 11, wherein step (c) is conducted at a temperature of from about 100° C. to about 150° C.

14. The method of claim 11, wherein step (b) is conducted in an alkaline aqueous or non-aqueous solvent, at a pH from about 10 to about 14, a temperature from about 20° C. to about 100° C., and for a time of from about 30 minutes to about 24 h; and
    step (c) is conducted at a temperature of from about 100° C. to about 150° C.

15. A method to make N-acetyl-p-aminophenol from lignin, the method comprising:
    (a) performing an ammonia fiber expansion process reaction or an extractive ammonia process reaction on lignin to yield p-hydroxybenzamide;
    (b) converting at least a portion of the p-hydroxybenzamide from step (a) to p-aminophenol; and then
    (c) N-acetylating at least a portion of the p-aminophenol from step (b) to yield N-acetyl-p-aminophenol.

16. The method of claim 15, wherein, step (b) comprises contacting the p-hydroxybenzamide with a hypohalite salt to cause a Hofmann-style rearrangement reaction, thereby yielding p-aminophenol.

17. The method of claim 15, wherein step (c) comprises contacting the p-aminophenol with acetic anhydride and water for a time and at a temperature to yield N-acetyl-p-aminophenol.

18. The method of claim 15, wherein step (b) comprises contacting the p-hydroxybenzamide with a hypohalite salt to cause a Hofmann-style rearrangement reaction, thereby yielding p-aminophenol; and
    step (c) comprises contacting the p-aminophenol with acetic anhydride and water for a time and at a temperature to yield N-acetyl-p-aminophenol.

19. The method of claim 18, wherein step (b) is conducted in an alkaline aqueous or non-aqueous solvent, at a pH from about 10 to about 14, a temperature from about 20° C. to about 100° C., and for a time of from about 30 minutes to about 24 h.

20. The method of claim 18, wherein step (c) is conducted at a temperature of from about 100° C. to about 150° C.

21. The method of claim 18, wherein step (b) is conducted in an alkaline aqueous or non-aqueous solvent, at a pH from about 10 to about 14, a temperature from about 20° C. to about 100° C., and for a time of from about 30 minutes to about 24 h; and step (c) is conducted at a temperature of from about 100° C. to about 150° C.

* * * * *